United States Patent [19]

Matkovich et al.

[11] Patent Number: 5,252,222
[45] Date of Patent: Oct. 12, 1993

[54] FILTER FOR PARENTERAL SYSTEMS AND METHOD OF USING THEREOF

[75] Inventors: Vlado I. Matkovich; Thomas C. Gsell, both of Glen Cove; Thomas Bormann, Seaford, all of N.Y.

[73] Assignee: Pall Corporation, Glen Cove, N.Y.

[21] Appl. No.: 620,775

[22] Filed: Dec. 3, 1990

[51] Int. Cl.$^5$ ............ B01D 61/00; B01D 39/00
[52] U.S. Cl. .................. 210/650; 210/188; 210/321.64; 210/321.84; 210/436; 210/472; 210/489; 210/492; 210/503; 210/505; 210/508; 210/651; 210/653; 210/654; 604/405; 604/406
[58] Field of Search ............ 210/641, 650, 651, 653, 210/654, 188, 321.64, 321.84, 472, 489, 492, 503, 505, 507, 508, 435, 436; 604/405, 406

[56] References Cited

U.S. PATENT DOCUMENTS

| | | | |
|---|---|---|---|
| 3,246,767 | 4/1966 | Pall et al. | 210/505 |
| 3,353,682 | 11/1967 | Pall et al. | 210/505 |
| 3,803,810 | 4/1974 | Rosenberg | 55/159 |
| 4,203,848 | 5/1980 | Grandine, II | 210/490 |
| 4,340,479 | 7/1982 | Pall | 210/490 |
| 4,568,366 | 2/1986 | Frederick et al. | 210/436 |
| 4,618,533 | 10/1986 | Steuck | 428/315.7 |
| 4,701,267 | 10/1987 | Watanabe et al. | 210/505 |
| 4,702,840 | 10/1987 | Degen et al. | 210/638 |
| 4,707,266 | 11/1987 | Degen et al. | 210/638 |
| 4,886,836 | 12/1989 | Gsell et al. | 521/53 |
| 4,906,374 | 3/1990 | Gsell | 210/490 |
| 4,925,572 | 5/1990 | Pall | 210/767 |
| 4,954,256 | 9/1990 | Degen et al. | 210/490 |
| 4,964,989 | 10/1990 | Gsell | 210/490 |

OTHER PUBLICATIONS

Levchuk et al, "Method for Testing . . . Nutrient Admixtures", American Jornal of Hospital Pharmacy, vol. 45, pp. 1311-1321, 1988.
D'Angio et al, "The Growth of Microorganisms . . . Admixtures", Journal of Parenteral . . . Nutrition, vol. 11, No. 4, 1987.
Deitel, "Total Nutrient Admixtures . . . ", Oct. Dec., 1987, Jan. 1988.
Driscoll, "Clinical Issues . . . Nitrient Admixtures", DICP, The Annals of Pharmacology, vol. 24, Mar. 1990.
Rubin et al, "Use of 5-Micron . . . Parenteral Nutrition", Clinical Nutrition, No. 4, 1986, pp. 163-168.

*Primary Examiner*—Robert A. Dawson
*Assistant Examiner*—Sun Uk Kim
*Attorney, Agent, or Firm*—Leydig, Voit & Mayer

[57] ABSTRACT

A filter device and method are provided for treating parenteral nutrient fluids, particularly TNA systems containing lipids, glucose, and amino acids. The filter device comprises a housing and a microporous medium in the form of a synthetic polymeric microporous structure having a pore rating of less than 1.2 micrometers. A preferred microporous medium comprises, in series, a matrix of microfibers which has been radiation grafted to render the matrix wettable by parenteral nutrient fluids followed by a microporous membrane, also wettable by parenteral nutrient fluids, and having a finer pore rating than the microfibrous matrix.

26 Claims, 2 Drawing Sheets

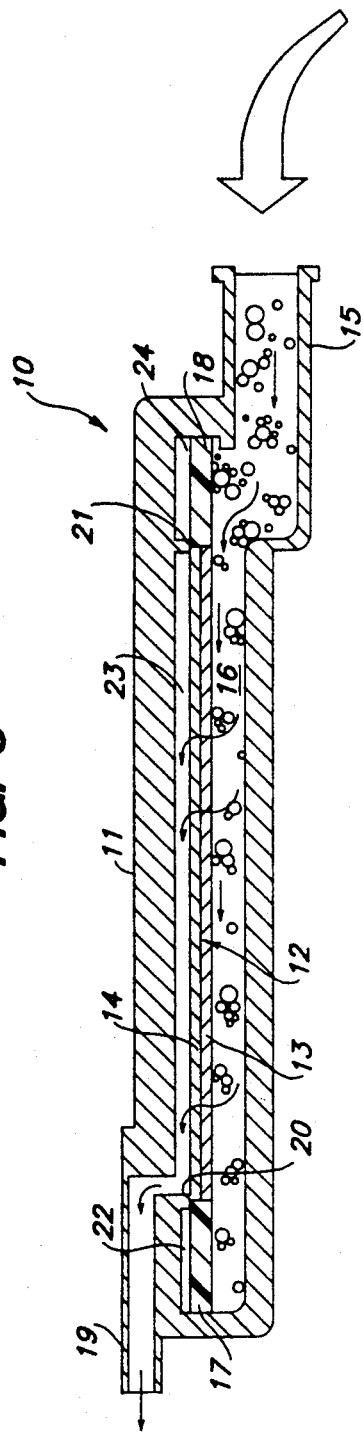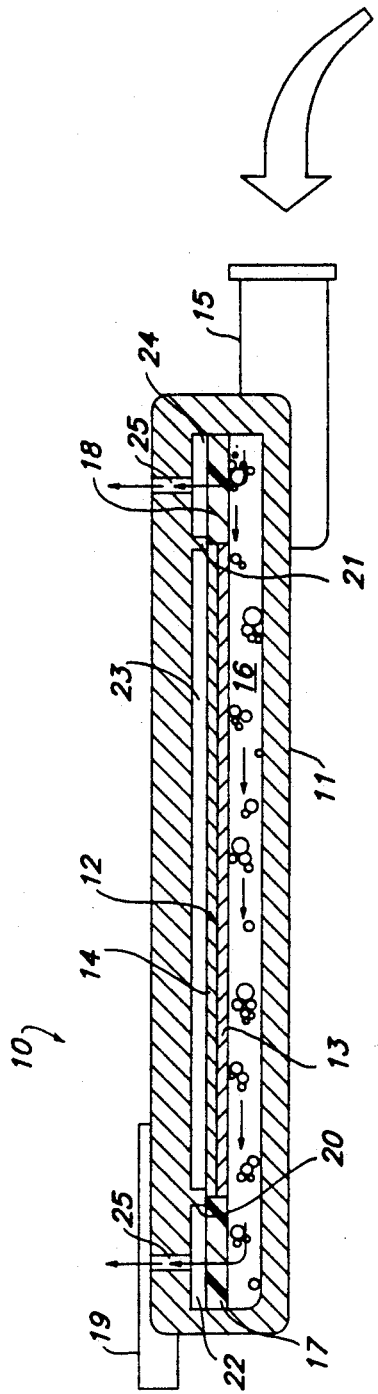

FILTER FOR PARENTERAL SYSTEMS AND METHOD OF USING THEREOF

TECHNICAL FIELD OF THE INVENTION

This invention relates to a filter device and method for treating parenteral fluids. More particularly, this invention relates to a filter device and method for treating parenteral nutrient admixtures.

BACKGROUND OF THE INVENTION

Individuals at risk of malnutrition or who are unable to obtain sufficient nutrients by enteral means must be fed intravenously. The use of total parenteral nutrition (TPN)—the administration of nutrients via a peripheral or central vein—has grown rapidly over the past several years. Unfortunately, infection is a potential major complication of TPN. This is of particular concern with malnourished an debilitated patients with compromised immune systems.

Microbiologic contamination of TPN mixtures may occur during preparation of the mixture, during administration, or via manipulation of the catheter. Accordingly, a total nutrient admixture (TNA) which contains all daily nutritional requirements in a single container is highly desirable because of the reduced likelihood of contamination due to the reduced number of manipulations of the intravenous delivery system. Reduced work loads of health care personnel are also a positive result of the use of single container TNA systems vis-a-vis conventional TPN systems requiring multiple nutrient containers. Typically, a TNA admixture contains three primary components: lipids in the form of an emulsion, glucose, and amino acids. Other components may include electrolytes, trace elements, and vitamins. The lipid emulsion is typically stabilized by an emulsifying agent such as a phospholipid which the filtering medium should not absorb.

While TNA systems offer the benefits noted above, one potential drawback is that the TNA system provides a better growth media for potentially pathogenic microorganisms. For example, the growth of fungal organisms, such as *Candida albicans*, in parenteral nutrient formulations poses an infectious threat because they are able to thrive in a variety of nutrient systems. Further, while *Candida albicans* has been shown to proliferate in both conventional TPN formulations and TNA admixtures, in at least one study growth was found to be stimulated in TNA admixtures. Similarly, studies have shown that TNA systems support bacterial growth significantly better than conventional TPN solutions.

In addition to the problems noted above, the lipid emulsion component results in the TNA admixture being opaque, making proper inspection of the mixture impossible. This may lead to a variety of problems including undetected fat particles having a size ranging from a few to as large as about 20 micrometers in diameter, creating the danger of fat embolus.

While problems with TNA systems have been recognized for some time, the benefits of such systems have been found to outweigh the attendant difficulties and their use has grown at a rapid rate. At present, in the vicinity of 80% of all TPN deliveries in Western Europe are in the form of TNA. The use of TNA systems also continues to expand in both the United States and Japan. Accordingly, there is an ongoing and growing need for means to alleviate difficulties with the use of TNA systems.

Attempts to alleviate the problems associated with TNA systems have focused on the use of membrane filters with pore ratings of 1.2 micrometers. While such filters are presently being used, they suffer from limitations. Specifically, such filters have limited flow capacity such that they exhibit excessive pressure buildup and plugging with concomitant limited onstream filter life. Excessive pressure build up is a serious problem with parenteral nutrient systems since the liquid nutrient is typically administered using a pump designed only to operate at relatively low pressures, e.g., less than 25 psi, typically less than 15 psi, and, in many applications, at less than 10 psi. Because these pumps are not engineered to operate at higher pressures, the parenteral fluid administration system typically includes an occlusion alarm which shuts down the pump at a relatively low pressure. Accordingly, excessive pressure build up and plugging of a filter device is a potentially serious problem. Additionally, membrane filters with pore ratings of 1.2 micrometers provide only limited ability to remove fine particulate and microbiological contaminants.

There is, therefore, a need for a filter device having an enhanced capability for filtration of fine particulate matter and microorganisms and having the capability of removing significant amounts of bacteria, the capacity to remove pyrogenic matter, such as bacterial endotoxins, and which, in addition, has a relatively high volumetric capacity, typically up to 3 liters of TNA at a flow rate of up to about 300 milliliters per hour, coupled with low pressure drop and, thus, good onstream life. Ideally, such a device would also have a relatively small hold up volume of about 5 cubic centimeters or less.

SUMMARY OF THE INVENTION

In accordance with the invention, a filter device for treating parenteral nutrient fluids, more particularly lipid-containing parenteral nutrient fluids, is provided comprising a housing including an inlet and an outlet and defining a fluid flow path between the inlet and the outlet and a liquid filtration element comprising a synthetic, polymeric microporous structure having a pore rating of less than 1.2 micrometers positioned inside the housing across the flow path.

In a preferred device, the microporous liquid filtration element comprises first and second filter media in series. The first or upstream microporous medium is preferably a matrix of microfibers followed by a second or downstream microporous medium with a finer pore rating than the first medium and less than 1.2 micrometers, both media preferably being wettable by the parenteral nutrient fluid. Additionally, a preferred device also comprises one or more non-wetting or liquid-repellant microporous structures to provide for gas/liquid separation via gas venting.

In accordance with the invention, parenteral nutrient fluid, more particularly lipid-containing parenteral nutrient fluids such as TNA admixtures, is treated by passing it through a liquid filtration element comprising a synthetic, polymeric microporous structure having a pore rating of less than 1.2 micrometers. Preferably, the element comprises first and second filter media in series with the second or downstream filter medium having a pore rating of less than 1.2 micrometers and being finer than that of the upstream medium.

BRIEF DESCRIPTION OF THE DRAWINGS

In the accompanying drawings:

FIG. 3 is a longitudinal sectional view taken along the line III—III of the device of FIG. 1; and FIG. 4 is a cross-sectional view taken along the line IV—IV of the device of FIG. 1.

DETAILED DESCRIPTION OF EMBODIMENTS

Figure 1:
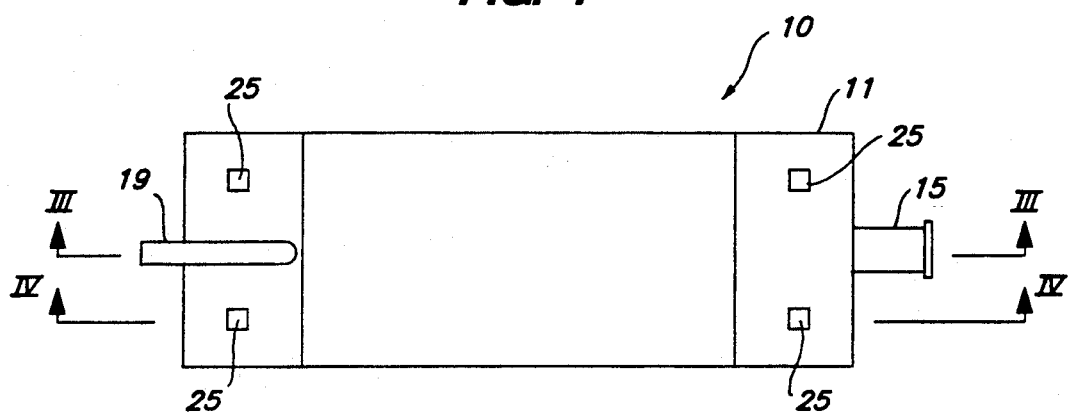
FIG. 1 is a top plan view of a filter device embodying the invention in which there are two liquid-repellant structures, one on each side of a liquid filtration element.

A filter device for treating parenteral fluids embodying the invention generally comprises a housing including an inlet and an outlet and defining a fluid flow path between the inlet and the outlet and a liquid filtration element comprising a synthetic, polymeric microporous structure positioned inside the housing across the flow path. In a preferred embodiment of the filter device, the liquid filtration medium is wettable by the parenteral fluid and is comprised of first and second media, the filter device further comprising a microporous non-wetting or liquid-repellant component to provide for gas/liquid separation.

The liquid filtration element preferably comprises two media in series. The first or upstream medium is characterized by a pore rating of greater than that of the second or downstream medium. Preferably, the first medium comprises a synthetic polymeric microfibrous matrix. The first medium is preferably wettable by the parenteral fluid. A preferred way of rendering the first medium wettable is by covering the surfaces of the medium with a grafted superstrate polymer (that is, a layer of polymer formed at and covering the surfaces of the medium) to render the medium wettable by the liquid with which it comes in contact in carrying out the method of this invention.

The second or downstream medium is characterized by a pore rating of less than 1.2 micrometers. In a preferred embodiment, the second medium comprises a microporous structure having a pore rating of less than about 1.0 micrometer, more preferably in the range of from about 0.5 to about 0.8 micrometer. As with the first medium, it is preferred that the second medium be wettable by the parenteral fluids with which it comes in contact. A variety of synthetic, polymeric, microporous structures may be used as the second or downstream medium provided they do not adversely affect the parenteral fluid being filtered, e.g., by releasing harmful components into the fluid, and they have the requisite physical properties to provide the desired filtration characteristics. Preferred materials include skinless, hydrophilic, microporous, polyamide membranes of the type described in U.S. Pat. 4,340,479. Particularly preferred are skinless, hydrophilic, microporous nylon 66 membranes of this type available from Pall Corporation under the trademark ULTIPOR ®. Microporous polyvinylidene difluoride membranes of the type disclosed in U.S. Pat. Nos. 4,203,848 and 4,618,533 may also be used as may microporous media with low non-specific protein adsorption, such as those described in U.S. Pat. Nos. 4,886,836, 4,906,374, and 4,964,989. Charge-modified polyamide membranes with a positive zeta potential in alkaline media, such as those described in U.S. Pat. No. 4,702,840 and available from Pall Corporation under the trademark BIODYNE B ® may also be used. Polyamide membranes with controlled surface properties such as those described in U.S. Pat. No. 4,707,266, as well as other microporous, synthetic, polymeric structures with the requisite pore rating including microfibrous matrices, may also be used. Each of the patents referred to above is incorporated herein by reference.

As noted above, it is preferred that the liquid filtration element be wettable by the parenteral nutrient fluid. In those instances where the medium is not wettable by the parenteral nutrient fluid, it may be rendered wettable by any method which does not adversely affect the filtration process. In addition to radiation grafting, suitable surface active agents, such as polyether polyhydroxy block copolymers, may be employed.

The liquid filtration element of the present invention is preferably in the form of a flat web or sheet, although other forms including pleated, cylindrical, or other geometric shapes suitable for incorporation into a filter may be used. When the liquid filtration element comprises first and second media, a composite filter sheet may be formed and used as a flat, planar sheet. Alternatively, the composite sheet may be formed into a pleated or accordion form and used in that form. As another less preferable alternative, the first and second filter media can be formed as separate sheets which can be used independently in a series arrangement. The liquid filtration element has a pore rating of less than 1.2 micrometers, preferably less than about 1.0 micrometer, more preferably from about 0.5 to about 0.8 micrometer. Particularly preferred as a second or downstream medium are hydrophilic microporous nylon 66 membranes with a pore rating of about 0.65 micrometers.

A microfibrous matrix, as the term is used herein, indicates a three-dimensional network of interconnected fibers, whether melt-blown, staple, or continuous, which together form a coherent structure suitable for use as a filter medium. Preferred microfibrous matrices are made from melt-blown thermoplastic polymeric fibers, such as polyolefins, particularly polypropylene, polyesters, particularly polybutylene terephthalate, and polyamides, such as nylon 66, where the fiber diameter is typically in the range of from about 1 to about 4 micrometers, typically having void volumes ranging from about 60 to about 90% and thicknesses in the range of from about 0.005 to about 0.10 inch.

While a liquid filtration element comprising two media is preferred, the element may consist of a single medium. When a single medium is used, a microfibrous matrix is preferred because of the enhanced dirt capacity of such a structure vis-a vis a microporous membrane formed from a synthetic plastic material having a continuous matrix structure and which has, relative to a microfibrous matrix, relatively uniform pore sizes and limited dirt capacity, making it more prone to pressure build up and clogging.

Pore ratings, as that term is used herein, may be determined using the Latex Sphere Test. This test determines the removal rating of a filtration medium by measuring the efficiency of the medium in removing uniform diameter polystyrene microspheres in a liquid medium. Typically, a dilute suspension of spheres (0.01 to 0.1 weight percent) is prepared in water containing 0.1 weight percent Triton X-100, an octyl phenoxypolyethoxyethanol with about nine and one-half ethylene oxide units per molecule, available from Rohm & Haas Company. The size of the spheres can vary from about 0.038 to about 5 microns. They are commercially available from Dow Chemical Company. A volume of about 10 cubic centimeters of the suspension per square inch (of the filtration medium) is passed through the medium and the filtrate is collected in a test tube. The concentration of microspheres in the filtrate can be measured by any number of means, for example, visually, or by use of a nephelometry device (i.e., turbidity meter). The smallest diameter microsphere which is retained at a 99.9% efficiency, i.e., 999 out of 1,000, determines the pore rating.

The filter device of the subject invention preferably further comprises a liquid-repellant or non-wetting component or structure acting in concert with the liquid filtration element which, as noted above, is preferably wetted by the parenteral nutrient liquid.

Any liquid-repellant or non-wetting porous material may be used which is effective in repelling and, therefore, does not pass a liquid under the conditions encountered in carrying out the method of this invention, thereby providing for venting of gas which may be present in the parenteral nutrient fluid to be filtered. Generally, the pore size of such a material should be less than about 15 micrometers. To preclude bacteria from entering the device via the liquid-repelling structure of the filter device (which in use must be open to the atmosphere to allow the gas to be vented), the pore size should be less than about 0.3 micrometer, preferably 0.2 micrometer or less. Preferred materials are the liquid-repelling membranes disclosed in U.S. Pat. No. 4,954,256. These membranes have a critical wetting surface tension (CWST) of less than about 28 dynes/centimeter, rendering them liquid-repelling or nonwetting by liquids with surface tensions well below that of water's surface tension of 72 dynes/centimeter. CWST is defined in U.S. Pat. No. 4,954,256, and in greater detail in U.S. Pat. No. 4,925,572, both of which are incorporated herein by reference. Of these, particularly preferred is a microporous, polymeric membrane having a pore rating of about 0.2 micrometer comprising a nylon 66 membrane substrate to which has been bonded to the surface a superstrate fluoropolymer formed from a monomer containing an ethylenically unsaturated group and a fluoroalkyl group.

The housings for the porous medium can be fabricated from any suitably impervious material, including any impervious thermoplastic material. For example, the housing may preferably be fabricated by injection molding from a transparent or translucent polymer, such as an acrylic, polystyrene, or polycarbonated resin. Not only is such a housing easily and economically fabricated, but it also allows observation of the passage of the fluid through the housing.

Figure 2:
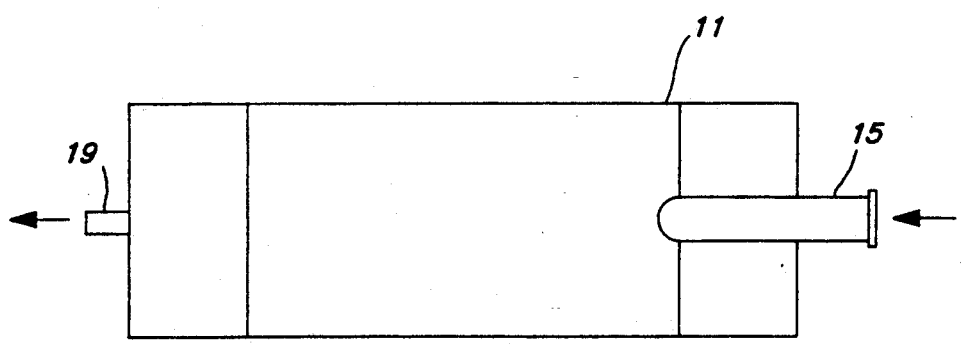
FIG. 2 is a bottom plan view of the filter device of FIG. 1.

The filter device in accordance with this invention may be fashioned in a variety of configurations including those described in U.S. Pat. No. 3,803,810 which is incorporated herein by reference. Preferably, the device will have a hold up volume of 20 cubic centimeters or less. A preferred configuration, as depicted in FIGS. 1-4, can be constructed with a hold up volume of less than 5 cubic centimeters. Indeed, a device as described in FIG. 1-4 was used in Example 1 below which had a hold up volume of only about 1.5 cubic centimeters.

Referring, then, to the drawings, a preferred general configuration is shown in FIGS. 1-4 which depict, in schematic form, the components of a filter device in accordance with the invention and which show the flow paths of the liquid and of gas which is separated from the liquid and vented to the atmosphere.

In FIGS. 1 to 4, a filter device 10 embodying the invention generally comprises a transparent housing 11 and a liquid filtration element 12 positioned within the housing 11. In the liquid filtration element depicted in the drawings, the liquid filtration element 12 comprises a first filter medium 13 and a second filter medium 14 in flat, planar composite filter sheet form.

The housing may have a variety of configurations. Preferably, liquid hold up volume is minimized. As depicted in the drawings, in a preferred device, an inlet 15 communicates with a first chamber 16 which is in fluid communication with the liquid filtration element 12 as well as with two nonwetting or liquid-repellant microporous structures 17 and 18 which allow gas to be vented from the device.

The housing 11 includes an inlet 15 and an outlet 19 defining a fluid flow path between the inlet 15 and the liquid outlet 19 with the liquid filtration element 12 disposed across the liquid flow path. The inlet and outlet may be variously configured. For example, the inlet 15 may be configured as a spike which can be inserted into a container of parenteral fluid. Alternatively, as shown in the drawings, both the inlet and the outlet can be configured as tube connectors. In addition to the chamber 16 depicted in FIGS. 3 and 4, the housing 11 has interior walls 20 and 21 which, in combination with the exterior walls for the housing 11, the liquid-repellant, microporous structures 17 and 18, and the liquid filtration element 12, define three additional chambers 22, 23, and 24. Chambers 22 and 24 include gas vents or outlets 25 for venting to the atmosphere gas separated from the incoming parenteral nutrient fluid.

The flow of parenteral nutrient liquid in the filter device 10 after entry of the parenteral nutrient fluid via the inlet 15 is depicted in FIG. 3 by arrows in the chambers 16 and 23. As depicted in FIG. 3, the liquid component of the parenteral fluid entering inlet 15 passes into the chamber 16, then through the liquid filtration element 12 into chamber 23, and then flows out of the filter device via the outlet 19.

The flow path of gas that may be present in the incoming parenteral nutrient fluid is depicted in FIG. 4 by arrows in chambers 16, 22, and 24. As depicted, the gas enters the chamber 16 and passes freely through the non-wetting or liquid-repellant structures 17 and 18 into the chambers 22 and 24 and then out the gas outlets or vents 25.

The invention will be better understood by reference to the following examples which are offered by way of illustration and not by way of limitation.

EXAMPLES

Example 1

A microfibrous matrix comprised of approximately 1.6 micrometer diameter polypropylene fibers having a basis weight of 4.5 milligrams per square centimeter was prepared by melt blown fiber extrusion. A final web thickness of about 0.003 inch was achieved by hot calendering using commercially available calendering equipment. The microfiber web was then surface modified in order to render hydrophilic. Gamma radiation (Cobalt 60) was used to graft co-polymerize hydroxypropyl acrylate and methacrylic acid in a monomer ratio of 9:1 with the polypropylene fiber surface and render the matrix wettable by a TNA parenteral admixture. A liquid filtration element in the form of a flat sheet comprising two layers of this grafted web and having a pore rating of 0.8 micrometer was assembled into the device described (in FIG. 1) which had a hold up volume of about 1.5 cubic centimeters and an effective liquid filtration surface area of about 1.7 square inches. The two non-wetting or liquid-repellant structures were polytetrafluoroethylene membranes with a nominal pore rating of 0.1 micrometer, each of about 0.15 square inch (0.97 square centimeter). This device was then subjected to a filtration test using 2.7 liters of a typical central formula TNA admixture which contained amino acid, dextrose, a lipid emulsion, a multivitamin solution, and electrolytes. Flow was provided by means of a peristaltic pump at a rate of 300 milliliters per hour, and the upstream applied pressure (effectively the pressure drop across the liquid filtration element) was monitored by means of a gauge upstream of the filter device. Throughout the duration of the test (2.7 liters total volume), the pressure did not rise significantly and remained between 8 and 9 psi.

Example 2

A microporous polyvinylidene fluoride (PVDF) membrane was solution cast under conditions which produced a 0.65 micrometer pore rating in its dry, unmodified state. A liquid filtration element in the form of a disc having a diameter of 1.125 inches was cut from this membrane and assembled into a reusable plastic housing jig having an effective flow area of 0.77 square inch. The membrane was prewetted in isopropyl alcohol prior to use since it was not wetted spontaneously by the TNA solution. The membrane was then tested for the filtration of TNA formulation of the same composition and in the same manner as in Example 1 except that flow was provided by means of a volumetric infusion pump (Model IMED 960 available from IMED Corporation) and the flow was adjusted to 150 milliliters per hour. During this test, the pressure was observed to increase steadily. At 170 milliliters of total volume throughput, the upstream pressure exceeded 15 psi, the pump alarm sounded, and the pump shut down, ending the test.

Example 3

The filtration test of Example 2 was repeated except that a prefilter consisting of a surface modified, polybutylene terephthalate polyester microfiber matrix microporous medium was positioned as a prefilter in the housing upstream of the downstream or second filter medium (PVDF membrane). The microfiber matrix was modified using a mixture of hydroxyethyl methacrylate and methacrylic acid in a monomer ratio of 0.35:1 using gamma radiation from a Cobolt 60 source. The prefilter had a voids percent of about 72%, a CWST equal to 94 dynes per centimeter rendering it readily wettable by the TNA formulation, an average fiber diameter of 2.4 micrometers, and a pore rating of about 2 micrometers. After prewetting of the PVDF membrane as in Example 2, a filtration test was run using a portion of the same TNA formulation used in Example 2. The same flow rate as in Example 2, 150 milliliters per hour, was also used. In contrast to Example 2, 620 milliliters of TNA solution were filtered without exceeding a pressure of about 7 psi. In particular, the pressure leveled off at about 6 psi after 170 milliliters of TNA had been filtered and remained relatively constant for the entire remaining volume of filtered TNA admixture. The results clearly demonstrates the beneficial effect of the prefilter section which resulted in a significantly lower applied pressure and thus a larger volume filtered.

Example 4

A nylon 66 membrane having a pore rating of 0.65 micrometer was tested in the same manner as was used in Example 2 except that the TNA admixture did not contain multi-vitamins and no prefilter section was utilized. The results showed the pressure drop to rise consistently as the TNA formulation was filtered. After 270 milliliters volume of throughput, the pressure exceeded 15 psi and the pump stopped.

Example 5

The same TNA admixture was used as in Example 4 to test the membrane and prefilter combination described below and the same test method was also used. The prefilter was the same as that used in Example 3 and the membrane was the same as the nylon 66 membrane used in Example 4. The results showed that the pressure drop leveled off at about 4.5 psi and did not rise significantly (only about 1 psi) over the test period during which a total volume of 1.5 liters was filtered. A comparison of Examples 4 and 5 reveals the benefit of the prefilter in the latter example which greatly extends the volume of the TNA admixture that can be filtered without excessive pressure build up.

Examples 4 and 5 demonstrate the benefits derived from the use of a prefilter.

A particularly preferred filter device in accordance with the subject invention has the configuration depicted in FIGS. 1-4 and utilizes a hydrophilic nylon membrane with a pore rating of about 0.65 micrometer in combination with a prefilter as described in Example 3 above and two non-wetting or liquid-repellant structures of a nylon 66 membrane having a CWST of less than 28 and a pore rating of about 0.2 micrometer. Preparation of such a liquidrepellant membrane is described in U.S. Pat. No. 4,954,256.

While the invention has been described in some detail by way of illustration and example, it should be understood that the invention is susceptible to various modifications and alternative forms and is not restricted to the specific embodiments set forth in the Examples. It should also be understood that these Examples are not intended to limit the invention but, on the contrary, the intention is to cover all modifications, equivalents, and alternatives falling within the spirit and scope of the invention.

We claim:

1. A filter device for treating parenteral nutrient fluid containing a lipid comprising:
   a housing including an inlet and an outlet and defining a fluid flow path between the inlet and the outlet;
   a liquid filtration element positioned within the housing across the flow path comprising first and second filter media;
   the first medium comprising a synthetic polymeric microporous microfibrous matrix having a pore rating greater than the second medium;
   the second medium comprising a microporous membrane having a pore rating of less than 1.2 micrometers; and
   wherein the liquid filtration element is adapted to remove fine particulate and biological contaminants from the parenteral nutrient fluid.

2. The filter device of claim 1 wherein the liquid filtration element is wettable by a parenteral nutrient fluid and the filter device further comprises a nonwetting, liquid repellant, microporous structure positioned inside the housing and adapted to separate gas from the parenteral nutrient fluid.

3. The filter device of claim 1 wherein the liquid filtration element is adapted to remove fine particulate and biological contaminants from the parenteral nutrient fluid with a pressure drop of about 15 psi or less while passing the parenteral nutrient fluid at a flow rate of up to about 300 milliliters per hours.

4. The filter device of claim 1 wherein the microfibrous matrix comprises thermoplastic polymeric fibers selected from the group consisting of polyolefins, polyesters, and polyamides, both the first and second medium being wettable by the parenteral nutrient fluid.

5. The filter device of claim 4 wherein the second medium has a pore rating of less than about 1.0 micrometer.

6. The filter device of claim 5 wherein the second medium has a pore rating in the range of from about 0.5 to about 0.8 micrometer.

7. The filter device of claim 6 wherein the microfibrous matrix comprises surface modified polybutylene terephthalate microfibers and the microporous membrane in nylon 66.

8. A filter device for treating parenteral nutrient fluid containing a lipid comprising:
a housing including an inlet and an outlet and defining a fluid flow path between the inlet and the outlet;
a liquid filtration element positioned within the housing across the flow path comprising first and second filter media;
the first medium comprising a synthetic polymeric microporous microfibrous matrix having a pore rating greater than the second medium;
the second medium comprising a microporous membrane having a pore rating of less than 1.2 micrometers; and
wherein the liquid filtration element is adapted to remove fine particulate and biological contaminants from the parenteral nutrient fluid with a pressure drop of about 15 psi or less while passing the parenteral nutrient fluid at a flow rate of up to about 300 milliliters per hours; and
a non-wetting, liquid repellant, microporous structure positioned inside the housing and adapted to vent gas from the parenteral nutrient fluid.

9. The filter device of claim 8 wherein the microfibrous matrix comprises thermoplastic polymeric fibers selected from the group consisting of polyolefins, polyesters, and polyamides, both the first and second medium being wettable by the parenteral nutrient fluid.

10. The filter device of claim 9 wherein the second medium has a pore rating of less than about 1.0 micrometer.

11. The filter device of claim 10 wherein the second medium has a pore rating in the rang of from about 0.5 to about 0.8 micrometer.

12. The filter device of claim 11 wherein the microfibrous matrix comprises surface modified polybutylene terephthalate microfibers and the microporous membrane is nylon 66.

13. A method for treating parenteral nutrient fluid containing a lipid for administration comprising:
passing the parenteral fluid containing a lipid through a liquid filtration element comprising a synthetic polymeric microfibrous matrix, said element having a pore rating of less than 1.2 micrometers, and administering the parenteral fluid.

14. The method of claim 13 wherein passing the parenteral nutrient fluid through a liquid filtration element comprises passing a total nutrient admixture comprising lipids, glucose, and amino acids through the liquid filtration element.

15. The method of claim 13 further comprising passing the parenteral fluid through the filtration element with a pressure drop of about 15 psi or less while passing the parenteral nutrient fluid at a flow rate of up to about 300 per hour.

16. The method of claim 13 wherein the liquid filtration element comprises first and second media, the first medium including a synthetic polymeric microfibrous matrix and having a pore rating of greater than the second medium and the second medium has a pore rating of less than 1.2 micrometers.

17. The method of claim 16 wherein the second medium is a membrane with a pore rating of less than about 1.0 micrometer.

18. The method of claim 17 wherein the second medium has a pore rating in the range of from about 0.5 to about 0.8 micrometer.

19. A method for treating parenteral nutrient fluid containing a lipid for administration comprising:
passing the parenteral fluid containing a lipid through a liquid filtration element comprising a synthetic polymeric microporous structure having a pore rating in the range from about 0.5 to about 0.8 micrometers and administering the parenteral fluid.

20. A method for treating parenteral nutrient fluid containing a lipid for administration comprising:
passing the parenteral fluid containing a lipid through a liquid filtration element comprising a synthetic polymeric microporous structure having a pore rating of less than 1.2 micrometers and administering the parenteral fluid.

21. The method of claim 20 further comprising passing the parenteral fluid through the filtration element with a pressure drop of about 15 psi or less while passing the parenteral nutrient fluid at a flow rate of up to about 300 ml per hour.

22. The method of claim 20 further comprising separating gas from the parenteral nutrient fluid.

23. The method of claim 20 wherein passing the parenteral fluid through a liquid filtration element comprises passing a total nutrient admixture comprising lipids, glucose and amino acids through the liquid filtration element.

24. The method of claim 20 comprising passing the parenteral fluid through the liquid filtration element having a pore rating in the range of about 0.5 to about 0.8 micrometers.

25. The method of claim 20 wherein passing the parenteral fluid through a liquid filtration element comprises passing the parenteral nutrient fluid through a first medium and a second medium, the first medium having a pore rating greater than the second medium, and the second medium having a pore rating of less than 1.2 micrometers.

26. The method of claim 20 wherein passing the parenteral fluid through the second medium comprises passing the parenteral fluid through a membrane having a pore rating of less than about 1.0 micrometers.

* * * * *